United States Patent
Ishii et al.

(10) Patent No.: US 6,489,504 B2
(45) Date of Patent: Dec. 3, 2002

(54) MALIC ACID AND OXALACETIC ACID DERIVATIVES

(75) Inventors: Yasutaka Ishii, Takatsuki (JP); Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/801,648

(22) Filed: Mar. 9, 2001

(65) Prior Publication Data

US 2001/0056120 A1 Dec. 27, 2001

(30) Foreign Application Priority Data

Mar. 10, 2000 (JP) ........................ 2000-067680

(51) Int. Cl.⁷ .................. C07C 65/21; C07C 61/09; C07C 69/76; C07C 69/74

(52) U.S. Cl. .................. 560/55; 560/126; 560/127; 562/470; 562/509

(58) Field of Search ................. 560/127, 176, 560/55, 126; 562/509, 470

(56) References Cited

U.S. PATENT DOCUMENTS 3,646,132 A * 2/1972 Trecker et al. .............. 260/544

OTHER PUBLICATIONS

"Zur Synthese von 2–(1–Tetralyl)–und 2–[5–1 5,6,7,8–Tetrahydro)–chinolyl]–glycin" Reimann et al, Archive der Pharmazie. (1977) 310(2), pp. 102–109.*

* cited by examiner

Primary Examiner—Mukuno J. Shah
Assistant Examiner—Zachary C. Tucker
(74) Attorney, Agent, or Firm—Birch, Stewart, Kolasch & Birch, LLP

(57) ABSTRACT

A malic acid or oxalacetic acid derivative is represented by the following formula (1):

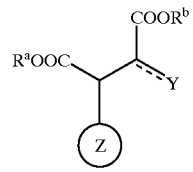

(1)

wherein ring Z is an alicyclic carbon ring; each of $R^a$ and $R^b$ is independently a hydrogen atom, a metal atom, or an organic group; and Y is a hydroxyl group or an oxygen atom, where ring Z is a bridged carbon ring or a monocyclic carbon ring having eight or more members when Y is an oxygen atom. The alicyclic carbon ring includes, for example, cyclooctane ring and adamantane ring. This compound is a novel malic acid derivative having an alicyclic group bonded to a carbon atom at the 3-position, or a novel oxalacetic acid derivative having a specific alicyclic group bonded to a carbon atom at the 3-position.

13 Claims, No Drawings

MALIC ACID AND OXALACETIC ACID DERIVATIVES

BACKGROUND OF THE INVENTION

1. Field of the Invention

The present invention relates to malic acid and oxalacetic acid derivatives which are useful as materials for pharmaceuticals, agricultural chemicals, and other fine chemicals and functional materials, and as optical resolution agents. Specifically, the invention relates to novel malic acid and oxalacetic acid derivatives having an alicyclic group bonded to a carbon atom at the 3-position.

2. Description of the Related Art

A compound having an alicyclic carbon ring such as adamantane ring particularly becomes a focus of attention in recent years, since it has completely distinguishable physical characteristics such as low toxicity and high transparency from those of a compound having an aromatic carbon ring such as benzene ring, although both have a ring.

Separately, malic acid and oxalacetic acid derivatives having a variety of substituents on a carbon atom at the 3-position, where a carbon atom to which a hydroxyl group or oxo group is bound is defined as the 2-position, are synthetically prepared and are used as fine chemicals and functional materials, or raw materials therefor. However, neither malic acid derivative having an alicyclic group bond to a carbon atom at the 3-position nor oxalacetic acid derivative having a bridged cyclic ring or a monocyclic alicyclic ring having eight or more members at the 3-position has been known.

SUMMARY OF THE INVENTION

Accordingly, it is an object of the present invention to provide a novel malic acid derivative having an alicyclic group bonded to a carbon atom at the 3-position and a novel oxalacetic acid derivative having a specific alicyclic group bonded to a carbon atom at the 3-position.

After intensive investigations to achieve the above objects, the present inventors found that a novel malic acid or oxalacetic acid derivative having an alicyclic group bound at the 3-position can be easily and efficiently produced by allowing an alicyclic hydrocarbon to react with maleic acid or fumaric acid derivative in the presence of the oxygen by the catalysis of an imide compound having a specific structure. The present invention has been accomplished based on these findings.

Specifically, the present invention provides a malic acid or oxalacetic acid derivative which is represented by the following formula (1):

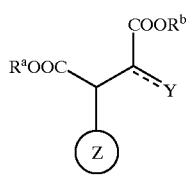

(1)

wherein ring Z is an alicyclic carbon ring; each of $R^a$ and $R^b$ is independently a hydrogen atom, a metal atom, or an organic group; and Y is a hydroxyl group or an oxygen atom, where ring Z is a bridged carbon ring or a monocyclic carbon ring having eight or more members when Y is an oxygen atom.

DESCRIPTION OF THE PREFERRED EMBODIMENTS

In the formula (1), Y is a hydroxyl group or an oxygen atom, and the bond between Y and the carbon atom is a single bond or double bond. When Y is a hydroxyl group, the compound represented by the formula (1) is malic acid (i.e., 2-hydroxysuccinic acid) or a derivative thereof. When Y is an oxygen atom, the compound represented by the formula (1) is oxalacetic acid (i.e., 2-oxosuccinic acid) or a derivative thereof.

Ring Z is an alicyclic carbon ring. Such alicyclic carbon rings include, but are not limited to, cyclopropane, cyclobutane, cyclopentane, cyclopentene, cyclohexane, cyclohexene, cycloheptane, cyclooctane, cyclooctene, cyclononane, cyclodecane, cyclododecane, cyclotetradecane, cyclohexadecane, and other monocyclic alicyclic carbon rings (cycloalkane rings and cycloalkene rings) each having about 3 to 30 members (preferably about 3 to 20 members, and more preferably about 5 to 20 members); perhydroindene ring, decalin ring, perhydrofluorene ring, perhydroanthracene ring, perhydrophenanthrene ring, perhydroacenaphthene ring, perhydrophenalene ring, pinane ring, bornane ring, norbornane ring, norbornene ring, norpinane ring, adamantane ring, tricyclo[5.2.1.0$^{2,6}$]decane ring, tetracyclo[4.4.0.1$^{2,5}$.1$^{7,10}$]dodecane ring, and other bridged carbon rings each having from two to six (preferably from two to four) rings. When ring Z is a bridged carbon ring, ring Z is bonded to the carbon atom indicated in the formula at the bridgehead position in many cases.

When Y is an oxygen atom, i.e., the compound represented by the formula (1) is an oxalacetic acid derivative, ring Z is a bridged carbon ring or a monocyclic carbon ring having eight or more members (e.g., about 8 to 30 members, and preferably about 8 to 20 members). Even when Y is a hydroxyl group, i.e., the compound represented by the formula (1) is a malic acid derivative, ring Z is preferably a bridged carbon ring or monocyclic carbon ring having eight or more members (e.g., about 8 to 30 members, and preferably about 8 to 20 members). Such a bridged carbon ring or a monocyclic carbon ring having eight or more members can impart preferred characteristics due to its rigidity and bulkiness to the compound.

The alicyclic carbon ring may have at least one substituent. Such substituents include, but are not limited to, halogen atoms (fluorine, chlorine, bromine, and iodine atoms), oxo group, hydroxyl group which may be protected with a protective group, a hydroxymethyl group which may be protected with a protective group, amino group which may be protected with a protective group, carboxyl group which may be protected with a protective group, substituted oxycarbonyl groups, substituted or unsubstituted carbamoyl groups, nitro group, acyl groups, cyano group, alkyl groups (e.g., methyl, ethyl, and other $C_1$–$C_4$ alkyl groups), cycloalkyl groups, aryl groups (e.g., phenyl and naphthyl groups), and heterocyclic groups. As the protective groups, conventional protective groups in the field of organic synthesis can be used.

The metal atom in $R^a$ and $R^b$ includes, but is not limited to, atoms of lithium, sodium, potassium, and other alkali metals; atoms of magnesium, calcium, barium, and other alkaline earth metals; and atoms of zinc and other transition metals.

The organic group in $R^a$ and $R^b$ includes, but is not limited to, hydrocarbon groups and heterocyclic groups. Such hydrocarbon groups include, for example, methyl, ethyl, propyl, isopropyl, butyl, isobutyl, s-butyl, t-butyl, hexyl, allyl, and other straight-chain or branched aliphatic hydrocarbon groups (alkyl groups, alkenyl groups, and alkynyl groups) each having about 1 to 20 (preferably about 1 to 10, and more preferably about 1 to 6) carbon atoms; cyclopropyl, cyclobutyl, cyclopentyl, cyclohexyl, cyclohexenyl, cyclooctyl, cyclodecyl, cyclododecyl, and other alicyclic hydrocarbon groups (e.g., cycloalkyl groups, cycloalkenyl groups, and bridged cyclic hydrocarbon groups) each having about 3 to 20 (preferably about 3 to 15) carbon atoms; phenyl, naphthyl, and other aromatic hydrocarbon groups each having about 6 to 14 carbon atoms. Heterocycles corresponding to the heterocyclic groups include, but are not limited to, furan ring, thiophene ring, pyridine ring, pyrrole ring, and other heterocycles each having an oxygen atom, sulfur atom or nitrogen atom as a hetero atom. Each of these hydrocarbon groups and heterocyclic groups may have at least one substituent (e.g., substituents which the alicyclic hydrocarbon group may have).

Typical examples of the compounds of the formula (1) in which Y is a hydroxyl group are, wherein the junction position of ring Z is defined as the 3-position, 3-cyclohexylmalic acid, 3-cyclooctylmalic acid, 3-cyclodecylmalic acid, 3-cyclododecylmalic acid, 3-cyclotetradecylmalic acid, and other 3-substituted malic acids in which ring Z is a monocyclic carbon ring, esters of these compounds (e.g., dimethyl esters, monomethyl esters, diethyl esters, monoethyl esters, diisopropyl esters, di-t-butyl esters, diallyl esters, and diphenyl esters), and salts of these compounds (e.g., sodium salts, potassium salts, and other alkali metal salts; and calcium salts, and other alkaline earth metal salts); 3-(1-adamantyl)malic acid, 3-(3,5-dimethyladamant-1-yl)malic acid, 3-(1-norbornyl)malic acid, 3-(tricyclo[5.2.1.0$^{2,6}$]decan-1-yl)malic acid, 3-(4a-decalinyl)malic acid, 3-(tetracyclo[4.4.0.1$^{2,5}$.1$^{7,10}$]ododecan-1-yl)malic acid, and other 3-substituted malic acid in which ring Z is a bridged carbon ring, esters of these compounds (e.g., the aforementioned esters), and salts of these compounds (e.g., the aforementioned salts).

Typical examples of the compounds of the formula (2) in which Y is an oxygen atom are, where the junction position of ring Z is defined as the 3-position, 3-cyclooctyloxalacetic acid, 3-cyclodecyloxalacetic acid, 3-cyclododecyloxalacetic acid, 3-cyclotetradecyloxalacetic acid, and other 3-substituted oxalacetic acids in which ring Z is a monocyclic carbon ring, esters of these compounds (e.g., dimethyl esters, monomethyl esters, diethyl esters, monoethyl esters, diisopropyl esters, di-t-butyl esters, diallyl esters, and diphenyl esters), and salts of these compounds (e.g., sodium salts, potassium salts, and other alkali metal salts; and calcium salts, and other alkaline earth metal salts); 3-(1-adamantyl)oxalacetic acid, 3-(3,5-dimethyladamant-1-yl)oxalacetic acid, 3-(1-norbornyl)oxalacetic acid, 3-(tricyclo[5.2.1.0$^{2,6}$]decan-1-yl)oxalacetic acid, 3-(4a-decalinyl)oxalacetic acid, 3-(tetracyclo[4.4.0.1$^{2,5}$.1$^{7,10}$]dodecan-1-yl)oxalacetic acid, and other 3-substituted oxalacetic acids in which ring Z is a bridged carbon ring, esters of these compounds (e.g., the aforementioned esters), and salts of these compounds (e.g., the aforementioned salts).

[Production of Malic Acid or Oxalacetic Acid Derivative]

The invented compound represented by the formula (1) can be produced, for example, by allowing an alicyclic compound represented by the following formula (3):

(3)

wherein ring Z is an alicyclic carbon ring, to react, in the presence of oxygen, with a maleic acid or fumaric acid derivative represented by the following formula (4):

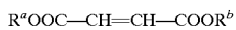

$R^a$OOC—CH=CH—COOR$^b$ wherein each of $R^a$ and $R^b$ is independently a hydrogen atom, a metal atom or an organic group, by the catalysis of an imide compound represented by the following formula (2):

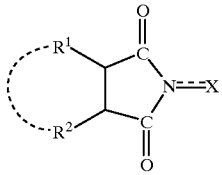

(2)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group; and one or two of N-substituted cyclic imido group indicated in the formula (2) may be further formed on $R^1$, $R^2$, or on the double bond or aromatic or non-aromatic ring formed together by $R^1$ and $R^2$.

Of the substituents $R^1$ and $R^2$ in the compound represented by the formula (2), the halogen atom includes iodine, bromine, chlorine and fluorine. The alkyl group includes, but is not limited to, methyl, ethyl, propyl, isopropyl, butyl, isobutyl, s-butyl, t-butyl, pentyl, hexyl, heptyl, octyl, decyl, and other straight- or branched-chain alkyl groups each having about 1 to 10 carbon atoms. Preferred alkyl groups are alkyl groups each having about 1 to 6 carbon atoms, of which lower alkyl groups each having about 1 to 4 carbon atoms are particularly preferred.

The aryl group includes, for example, phenyl and naphthyl groups. Illustrative cycloalkyl groups include cyclopentyl and cyclohexyl groups. Illustrative alkoxy groups are methoxy, ethoxy, propoxy, isopropoxy, butoxy, isobutoxy, t-butoxy, pentyloxy, hexyloxy, and other alkoxy groups each having about 1 to 10 carbon atoms. Preferred alkoxy groups are alkoxy groups having about 1 to 6 carbon atoms, of which lower alkoxy groups each having about 1 to 4 carbon atoms are particularly preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. Preferred alkoxycarbonyl groups are alkoxycarbonyl groups each having about 1 to 6 carbon atoms in the alkoxy moiety, of which lower alkoxycarbonyl groups each having about 1 to 4 carbon atoms in the alkoxy moiety are particularly preferred.

Illustrative acyl groups include, for example, formyl, acetyl, propionyl, butyryl, isobutyryl, valeryl, isovaleryl, pivaloyl, and other acyl groups each having about 1 to 6 carbon atoms.

The substituents $R^1$ and $R^2$ may be identical to or different from each other. The substituents $R^1$ and $R^2$ in the formula (2) may be combined to form a double bond, or an aromatic or non-aromatic ring. The preferred aromatic or non-aromatic ring has about 5 to 12 members, and particularly about 6 to 10 members. The ring may be a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring, and other aromatic rings (including condensed rings) which may have a substituent. The ring is composed of an aromatic ring in many cases. The ring may have at least one substituent. Such substituents include, but are not limited to, alkyl groups, haloalkyl groups, hydroxyl group, alkoxy groups, carboxyl group, alkoxycarbonyl groups, acyl groups, nitro group, cyano group, amino group, and halogen atoms.

In the formula (2), X represents an oxygen atom or a hydroxyl group, and the bond between the nitrogen atom N and X is a single bond or a double bond.

One or two of N-substituted cyclic imido group indicated in the formula (2) may be further formed on $R^1$, $R^2$, or on the double bond or aromatic or non-aromatic ring formed together by $R^1$ and $R^2$. For example, when $R^1$ or $R^2$ is an alkyl group having two or more carbon atoms, the N-substituted cyclic imido group may be formed together with the adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or non-aromatic ring, the N-substituted cyclic imido group may be formed with the adjacent two carbon atoms constituting the ring.

Preferred imide compounds include compounds of the following formulae:

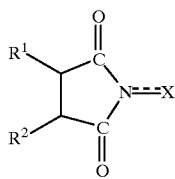
(2a)

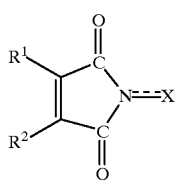
(2b)

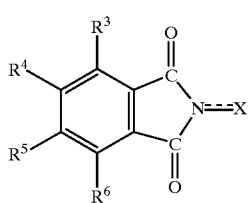
(2c)

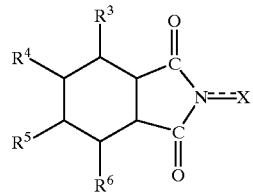
(2d)

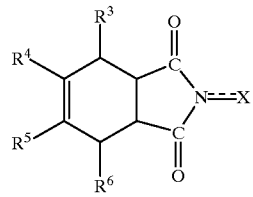
(2e)

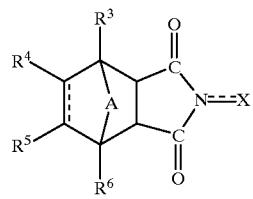
(2f)

wherein each of $R^3$ to $R^6$ is, identical to or different from one another, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^3$ to $R^6$ may be combined to form an aromatic or non-aromatic ring;, A in the formula (2f) is a methylene group or an oxygen atom; and $R^1$, $R^2$ and X have the same meanings as defined above, where one or two of N-substituted cyclic imido group indicated in the formula (2c) may be further formed on the benzene ring in the formula (2c).

In the substituents $R^3$ to $R^6$, the alkyl group includes similar alkyl groups to those exemplified above, of which alkyl groups each having about 1 to 6 carbon atoms are particularly preferred. The haloalkyl group includes trifluoromethyl group, and other haloalkyl groups each having about 1 to 4 carbon atoms. The alkoxy group includes similar alkoxy groups to those mentioned above, of which lower alkoxy groups each having about 1 to 4 carbon atoms are particularly preferred. The alkoxycarbonyl group includes similar alkoxycarbonyl groups to those described above, of which lower alkoxycarbonyl groups each having about 1 to 4 carbon atoms in the alkoxy moiety are particularly preferred. The acyl group includes similar acyl groups to those described above, of which acyl groups each having about 1 to 6 carbon atoms are particularly preferred. The illustrative halogen atoms include fluorine, chlorine and bromine atoms. Each of the substituents $R^3$ to $R^6$ is often a hydrogen atom, a lower alkyl group having about 1 to 4 carbon atoms, a carboxyl group, a nitro group, or a halogen atom. The ring formed together by $R^3$ to $R^6$ includes similar rings to the aforementioned rings which are formed together by $R^1$ and $R^2$. Among them, aromatic or non-aromatic 5- to 12-membered rings are particularly preferred.

Typically preferred imide compounds include, for example, N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds represented by the formula (2) can be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

Such acid anhydrides include, but are not limited to, succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are particularly preferred.

Each of the imide compounds of the formula (2) can be used alone or in combination. The imide compounds can be used as being supported on a carrier. As such carriers, activated carbon, zeolite, silica, silica-alumina, bentonite, and other porous carries are frequently employed.

The proportion of the imide compound can be selected within a wide range and is, for example, about 0.0001 to 1 mole, preferably about 0.001 to 0.5 mole, more preferably about 0.01 to 0.4 mole, and often about 0.05 to 0.35 mole, relative to 1 mole of the compound used in less amount of the compound of the formula (3) and the compound of the formula (4).

In the above process, a metallic compound may be used as a promoter (co-catalyst) in combination with the imide compound. The combination use of the imide compound with a metallic compound can improve the rate and selectivity of the reaction.

Metallic elements constituting the metallic compounds are not specifically limited and any of metallic elements of the Groups 1 to 15 of the Periodic Table of Elements can be used. The term "metallic element" as used in the present invention also means and includes boron B. Such metallic elements include, but are not limited to, Group 1 elements (e.g., Li, Na and K), Group 2 elements (e.g., Mg, Ca, Sr and Ba), Groups 3 elements (e.g., Sc, lanthanoid elements and actinoid elements), Group 4 elements (e.g., Ti, Zr and Hf), Group 5 elements (e.g., V), Group 6 elements (e.g., Cr, Mo and W), Group 7 elements (e.g., Mn), Group 8 elements (e.g., Fe and Ru), Group 9 elements (e.g., Co and Rh), Group 10 elements (e.g., Ni, Pd and Pt), Group 11 elements (e.g., Cu), Group 12 elements (e.g., Zn), Groups 13 elements (e.g., B, Al and In), Group 14 elements (e.g., Sn and Pb), Group 15 elements (e.g., Sb and Bi), of the Periodic Table of Elements,. Preferred metallic elements include transition metal elements (elements of Groups 3 to 12 of the Periodic Table of Elements). Among them, elements of the Groups 5 to 11 of the Periodic Table of Elements are preferred, of which elements of Group 6, Group 7 and Group 9 are typically preferred. Especially, V, Mo, Co and Mn are preferred. The valence of the metallic element is not particularly limited and is about 0 to 6 in many cases.

Such metallic compounds include, but are not limited to, elementary substances, hydroxides, oxides (including complex oxides), halides (fluorides, chlorides, bromides and iodides), salts of oxoacids (e.g., nitrates, sulfates, phosphates, borates and carbonates), oxoacids, isopolyacids, heteropolyacids, and other inorganic compounds of the aforementioned metallic elements; salts of organic acids (e.g., acetates, propionates, prussiates, naphthenates and stearates), complexes, and other organic compounds of the metallic elements. Ligands constituting the complexes include, for example, OH (hydroxo), alkoxy (e.g., methoxy, ethoxy, propoxy and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aquo), phosphines (triphenylphosphine and other triarylphosphines) and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Specific examples of the metallic compounds include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; acetylacetonatocobalt, and other complexes, and other divalent or trivalent cobalt compounds. Illustrative vanadium compounds include, but are not limited to, vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valence of 2 to 5. Examples of molybdenum compounds include molybdenum hydroxide, molybdenum oxide, molybdenum chloride, molybdenum bromide, molybdenum sulfide, molybdic acid or its salts, phosphomolybdic acid or its salts, silicomolybdic acid or its salts, and other inorganic compounds; molybdenum carbonyl, bis(acetylacetonato)dioxomolybdenum, chlorotricarbonyl ($\eta$-cyclopentadienyl)molybdenum, dibromobis($\eta$-cyclopentadienyl)molybdenum, and other complexes, and other molybdenum compounds having a valence of 0 to 6. Examples of compounds of the other metallic elements include compounds corresponding to the above-mentioned cobalt, vanadium or molybdenum compounds. Each of these metallic compounds can be used alone or in combination. The combination use of a divalent metallic compound (e.g., a divalent cobalt compound) and a trivalent metallic compound (e.g., a trivalent cobalt compound) can particularly improve the yield and selectivity of the target compound.

The amount of the metallic compound is, for example, about 0.0001 to 0.7 mole, preferably about 0.001 to 0.5 mole, more preferably about 0.002 to 0.1 mole, and often about 0.005 to 0.05 mole, relative to 1 mole of the compound used in a less amount of the compound of the formula (3) and the compound of the formula (4).

Oxygen for use in the reaction can be any of molecular oxygen and nascent oxygen. As the molecular oxygen, pure oxygen or oxygen diluted with an inert gas such as nitrogen, helium, argon, or carbon dioxide can be used. Air is preferably used as the oxygen from the viewpoints of operating property and safety, as well as cost efficiency. In some cases, a gaseous mixture of oxygen with an inert gas such as nitrogen can provide a higher yield of the target product than the case where pure oxygen is used. Excess moles of oxygen can be used relative to the compound used in a less amount of the compound of the formula (3) and the compound of the formula (4).

An alicyclic compound corresponding to ring Z of the compound represented by the formula (1) is generally used as the alicyclic compound represented by the formula (3). Likewise, a maleic acid or fumaric acid derivative corresponding to $R^a$ and $R^b$ of the compound represented by the formula (1) is generally used as the maleic acid or fumaric acid derivative represented by the formula (4).

A reaction between the alicyclic compound represented by the formula (3) and the maleic acid or fumaric acid derivative represented by the formula (4) is generally performed in the presence of, or in the absence of, a solvent. Such solvents include, but are not limited to, acetic acid, propionic acid, and other organic acids; acetonitrile, propionitrile, benzonitrile, and other nitriles; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. In may cases, acetic acid and other organic acids, acetonitrile, benzonitrile, and other nitrites, trifluoromethylbenzene and other halogenated hydrocarbons, ethyl acetate and other esters are used as the solvent.

The ratio of the alicyclic compound represented by the formula (3) to the maleic acid or fumaric acid derivative represented by the formula (4) can be appropriately selected depending on the type (cost, reactivity) of the two compounds, or the combination thereof. For example, the compound of the formula (3) can be used in excess (e.g., about 2 to 50 times by mole) to the compound of the formula (4), and contrary to this, the compound of the formula (4) can be used in excess to the compound of the formula (3).

A reaction temperature can be appropriately selected depending on the types of the compound of the formula (3) and the compound of the formula (4) and the type of the target product, and is, for example, about 0° C. to 300° C., preferably about 20° C. to 200° C., and more preferably about 30° C. to 150° C. The reaction is often performed at a temperature of about 40° C. to 100° C. The reaction can be conducted at atmospheric pressure or under a pressure (under a load), and when the reaction is performed under a pressure, the pressure is usually about 1 to 100 atm (0.101 to 10.1 MPa), and preferably about 1.5 to 80 atm (0.152 to 8.08 MPa) . A reaction time can be appropriately selected within a range from, for example, about 30 minutes to 48 hours, depending on the reaction temperature and pressure.

The reaction can be performed in a batch system, semi-batch system, continuous system or another conventional system, in the presence of, or under the flow of, oxygen. After the completion of the reaction, reaction products can be easily separated and purified according to a conventional technique such as filtration, concentration, distillation, extraction, crystallization, recrystallization, column chromatography and other separation means, or any combination of these separation means.

According to the above process, it is considered that a malic acid derivative (Y is a hydroxyl group) of the compounds represented by the formula (1) is formed in the following manner. Specifically, in the alicyclic compound represented by the formula (3), a hydrogen atom (it is often a hydrogen atom at the bridgehead position when ring Z is a bridged carbon ring) indicated in the formula is drawn out to form a radical, and the radical attacks a carbon atom constituting the unsaturated bond of the maleic acid or fumaric acid derivative represented by the formula (4), and concurrently, oxygen attacks a radical which is secondarily formed at the adjacent position thereof to form the malic acid derivative. It is also considered that the aforementioned malic acid derivative is further oxidized in the system to thereby form an oxalacetic acid derivative (Y is an oxygen atom) of the compounds represented by the formula (1).

Of the compounds represented by the formula (1), a compound in which each of $R^a$ and $R^b$ is a hydrogen atom or a metal atom (acid or salt) can also be produced by subjecting a corresponding compound (ester) in which each of $R^a$ and $R^b$ is an organic group to acid or alkali hydrolysis in a conventional manner.

As described above, the present invention can provide a novel malic acid derivative having an alicyclic group bonded to a carbon atom at the 3-position and a novel oxalacetic acid derivative having a specific alicyclic group bonded to a carbon atom at the 3-position.

The present invention will now be illustrated in further detail with reference to several examples below, which are not intended to limit the scope of the invention.

EXAMPLE 1

A mixture of 3 mmol of dimethyl fumarate, 15 mmol of 1,3-dimethyladamantane, 0.6 mmol of N-hydroxyphthalimide, 0.03 mmol of acetylacetonatocobalt (III) [Co(acac)$_3$] and 8 ml of benzonitrile was stirred at 75° C. in an oxygen atmosphere [1 atm (=0.101 MPa)] for 2.5 hours. The resulting reaction mixture was concentrated and was purified by column chromatography on a silica gel to yield dimethyl 3-(3,5-dimethyladamant-1-yl)malate [dimethyl 2-hydroxy-3-(3,5-dimethyladamant-1-yl) succinate] in a yield of 65%, dimethyl 3-(3,5-dimethyladamant-1-yl)oxalacetate [dimethyl 3-(3,5-dimethyladamant-1-yl)-2-oxosuccinate] in a yield of 28%, 1-hydroxy-3,5-dimethyladamantane in a yield of 10%, 1,3-dimethyl-6-oxoadamantane in a yield of 4%, and 1,3-dihydroxy-5,7-dimethyladamantane in a yield of 4%, with a conversion from dimethyl fumarate of 99%.

[Spectral Data of Dimethyl 3-(3,5-Dimethyladamant-1-yl)malate]

$^1$H-NMR (CDCl$_3$) δ: 4,52 (dd, J=2.2, 9.9 Hz, 1H), 3.77 (s, 3H), 3.72 (s, 3H), 2.54 (d, J=2.2 Hz, 1H), 0.83 (s, 6H), 0.96–2.10 (m, 13H)

IR (NaCl) (cm$^{-1}$): 3500, 2945, 1750, 1450, 1160

[Spectral Data of Dimethyl 3-(3,5-Dimethyladamant-1-yl)oxalacetate]

$^1$H-NMR (CDCl$_3$) δ: 4.09 (s, 1H), 3.87 (s, 3H), 3.70 (s, 3H), 1.12–2.18 (m, 13H), 0.81 (s, 6H)

$^{13}$C-NMR (CDCl$_3$) δ: 189.2, 168.2, 162.7, 62.3, 53.3, 52.1, 50.6, 45.9, 45.8, 42.7, 39.1, 38.4, 31.3, 30.5, 29.5

IR (NaCl) (cm$^{-1}$): 2899, 1731, 1454, 1273, 1164

EXAMPLE 2

The procedure of Example 1 was repeated, except that 0.03 mmol of vanadyl acetylacetonato(II) [VO(acac)$_2$] was used instead of acetylacetonatocobalt(III) [Co(acac)$_3$], to yield dimethyl 3-(3,5-dimethyladamant-1-yl) malate in a yield of 11%, dimethyl 3-(3,5-dimethyladamant-1-yl) oxalacetate in a yield of 34%, 1-hydroxy-3,5-dimethyladamantane in a yield of 8%, 1,3-dimethyl-6-oxoadamantane in a yield of 5%, and 1,3-dihydroxy-5,7-dimethyladamantane in a yield of 4%, with a conversion from dimethyl fumarate of 92%.

EXAMPLE 3

The procedure of Example 1 was repeated, except that 0.03 mmol of cobalt(II) acetate was used instead of acetylacetonatocobalt(III) [Co(acac)$_3$], to yield dimethyl 3-(3,5-dimethyladamant-1-yl)malate in a yield of 64%, dimethyl 3-(3,5-dimethyladamant-1-yl)oxalacetate in a yield of 19%, 1-hydroxy-3,5-dimethyladamantane in a yield of 9%, 1,3-dimethyl-6-oxoadamantane in a yield of 5%, and 1,3-dihydroxy-5,7-dimethyladamantane in a yield of 3%, with a conversion from dimethyl fumarate of 99%.

EXAMPLE 4

The procedure of Example 1 was repeated, except that 0.03 mmol of acetylacetonatocobalt(II) [Co(acac)$_2$] was used instead of acetylacetonatocobalt(III) [Co(acac)$_3$], to yield dimethyl 3-(3,5-dimethyladamant-1-yl)malate in a yield of 65%, dimethyl 3-(3,5-dimethyladamant-1-yl) oxalacetate in a yield of 25%, 1-hydroxy-3,5-dimethyladamantane in a yield of 12%, 1,3-dimethyl-6-oxoadamantane in a yield of 6%, and 1,3-dihydroxy-5,7-dimethyladamantane in a yield of 4%, with a conversion from dimethyl fumarate of 99%.

EXAMPLE 5

The procedure of Example 1 was repeated, except that the reaction was performed in the atmosphere of a gaseous mixture of oxygen and nitrogen (molar ratio 1:1) [1 atm (=0.101 MPa)], to thereby yield dimethyl 3-(3,5-dimethyladamant-1-yl)malate in a yield of 68%, dimethyl 3-(3,5-dimethyladamant-1-yl)oxalacetate in a yield of 15%, 1-hydroxy-3,5-dimethyladamantane in a yield of 1%, 1,3-dimethyl-6-oxoadamantane in a yield of 2%, and 1,3-dihydroxy-5,7-dimethyladamantane in a yield of 2%, with a conversion from dimethyl fumarate of 99%.

EXAMPLE 6

A mixture of 3 mmol of dimethyl maleate, 27 mmol of 1,3-dimethyladamantane, 0.9 mmol of N-hydroxyphthalimide, 0.03 mmol of acetylacetonatocobalt (III) [Co(acac)$_3$] and 8 ml of acetonitrile was stirred at 75° C. in the atmosphere of a gaseous mixture of oxygen and nitrogen (molar ratio 1:1) [1 atm (=0.101 MPa)] for 14 hours. The resulting reaction mixture was concentrated and was purified by column chromatography on a silica gel to thereby yield dimethyl 3-(3,5-dimethyladamant-1-yl)malate in a yield of 61%, dimethyl 3-(3,5-dimethyladamant-1-yl) oxalacetate in a yield of 18%, 1-hydroxy-3,5-dimethyladamantane in a yield of 3%, 1,3-dimethyl-6-oxoadamantane in a yield of 2%, and 1,3-dihydroxy-5,7-dimethyladamantane in a yield of 1%, with a conversion from dimethyl maleate of 86%.

EXAMPLE 7

A mixture of 3 mmol of dimethyl fumarate, 30 mmol of cyclooctane, 0.6 mmol of N-hydroxyphthalimide, 0.06 mmol of acetylacetonatocobalt(III) [Co(acac)$_3$] and 10 ml of benzonitrile was stirred at 70° C. in an oxygen atmosphere [1 atm (=0.101 MPa)] for 14 hours. The resulting reaction mixture was concentrated and was purified by column chromatography on a silica gel to yield dimethyl 3-cyclooctylmalate [dimethyl 3-cyclooctyl-2-hydroxysuccinate] in a yield of 4%, dimethyl 3-cyclooctyloxalacetate [dimethyl 3-cyclooctyl-2-oxosuccinate] in a yield of 36%, cyclooctanol in a yield of 2%, cyclooctanone in a yield of 5%, and 1,4-cyclooctanedione in a yield of 1%, with a conversion from dimethyl fumarate of 98%.

[Spectral Data of Dimethyl 3-Cyclooctylmalate]
$^1$H-NMR (CDCl$_3$) δ: 4.41 (dd, J=3.3, 9.5 Hz, 1H), 3.83 (s, 3H), 3.77 (s, 3H), 3.36 (d, J=9.5 Hz, 1H), 2.70 (dd, J=3.3, 9.5 Hz, 1H), 1.33–2.24 (m, 15H)
$^{13}$C-NMR (CDCl$_3$) δ: 174.3, 173.8, 69.7, 54.4, 52.5, 51.8, 35.7, 30.2, 29.0, 27.1, 27.0, 26.2, 25.5, 24.9
IR (NaCl) (cm$^{-1}$) : 3500, 2945, 1743, 1447, 1162

[Spectral Data of Dimethyl 3-Cyclooctyloxalacetate]
$^1$H-NMR (CDCl$_3$) δ: 3.92 (s, 3H), 3.81 (s, 3H), 3.43 (s, 1H), 1.31–2.36 (m, 15H)
$^{13}$C-NMR (CDCl$_3$) δ: 190.2, 168.5, 163.1, 54.2, 52.1, 51.9, 35.7, 30.2, 29.1, 27.2, 27.0, 26.3, 25.4, 24.9
IR (NaCl) (cm$^{-1}$): 2898, 1735, 1452, 1270, 1161

EXAMPLE 8

A mixture of 3 mmol of dimethyl fumarate, 45 mmol of cyclohexane, 0.9 mmol of N-hydroxyphthalimide, 0.03 mmol of acetylacetonatocobalt(III) [Co(acac)$_3$], 0.015 mmol of acetylacetonatocobalt(II) [Co(acac)$_2$] and 8 ml of benzonitrile was stirred at 70° C. in the atmosphere of a gaseous mixture of oxygen and nitrogen (molar ratio 1:1) [1 atm (=0.101 MPa)] for 14 hours. The resulting reaction mixture was concentrated and was purified by column chromatography on a silica gel to thereby yield dimethyl 3-cyclohexylmalate [dimethyl 3-cyclohexyl-2-hydroxysuccinate] in a yield of 31%, dimethyl 3-cyclohexyloxalacetate [dimethyl 3-cyclohexyl-2-oxosuccinate] in a yield of 11%, cyclohexanol in a trace amount, and cyclohexanone in a yield of 2%, with a conversion from dimethyl fumarate of 93%.

[Spectral Data of Dimethyl 3-Cyclohexylmalate]
$^1$H-NMR (CDCl$_3$) δ: 4.41 (s, 1H), 3.77 (s, 3H), 3.68 (s, 3H), 3.45 (d, J=3.3 Hz, 1H), 2.61 (dd, J=3.3, 9.2 Hz, 1H), 1.03–1.98 (m, 13H)
$^{13}$C-NMR (CDCl$_3$) δ: 174.1, 173.8, 69.3, 54.2, 52.4, 51.8, 36.4, 31.5, 30.2, 26.2, 26.1, 26.0
IR (NaCl) (cm$^{-1}$) : 3500, 2930, 1746, 1434, 1166

[Spectral Data of Dimethyl 3-Cyclohexyloxalacetate]
$^1$H-NMR (CDCl$_3$) δ: 3.77 (s, 3H), 3.68 (s, 3H), 3.17 (s, 1H), 1.01–2.45 (m, 11H)
$^{13}$C-NMR (CDCl$_3$) δ: 198.7, 174.0, 173.8, 54.2, 52.4, 51.8, 36.2, 31.6, 30.1, 26.1, 26.0, 25.9
IR (NaCl) (cm$^{-1}$) 2930, 1746, 1434, 1166

EXAMPLE 9

A mixture of 3 mmol of dimethyl fumarate, 45 mmol of cyclohexane, 0.9 mmol of N-hydroxyphthalimide, 0.03 mmol of acetylacetonatocobalt(II) [Co(acac)$_2$] and 8 ml of benzonitrile was stirred at 70° C. in the atmosphere of a gaseous mixture of oxygen and nitrogen (molar ratio 1:1) [1 atm (=0.101 MPa)] for 14 hours. The resulting reaction mixture was concentrated and was purified by chromatography on a silica gel to thereby yield dimethyl 3-cyclohexylmalate [dimethyl 3-cyclohexyl-2-hydroxysuccinate] in a yield of 26%, dimethyl 3-cyclohexyloxalacetate [dimethyl 3-cyclohexyl-2-oxosuccinate] in a yield of 11%, cyclohexanol in a yield of 8%, cyclohexanone in a yield of 14%, and 4-methoxycarbonyl-3-hydroxy-2-oxo-1-oxaspiro[4.5]decane in a yield of 6%, with a conversion from dimethyl fumarate of 99%.

Other embodiments and variations will be obvious to those skilled in the art, and this invention is not to be limited to the specific matters stated above.

What is claimed is:

1. A malic acid or oxalacetic acid derivative represented by the following formula (1):

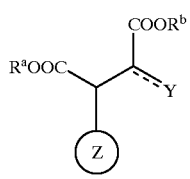

(1)

wherein each of $R^a$ and $R^b$ is independently a hydrogen atom, a metal atom, or a hydrocarbon or heterocyclic group; and ring Z is an alicyclic carbon ring when Y is a hydroxyl group or ring Z is a bridged carbon ring or a monocyclic carbon ring having eight or more members when Y is an oxygen atom.

2. The malic acid acid derivative of claim 1, represented by the following formula (1):

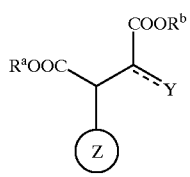

(1)

wherein each of $R^a$ and $R^b$ is independently a hydrogen atom, a metal atom, or a hydrocarbon or heterocyclic group; and ring Z is an alicyclic carbon ring when Y is a hydroxyl group.

3. The malic acid derivative of claim 2, wherein each of $R^a$ and $R^b$ is independently a hydrogen atom, a metal atom, a straight-chain or branched aliphatic hydrocarbon group having 1 to 20 carbon atoms, an alicyclic hydrocarbon group having 3 to 20 carbon atoms, an aromatic hydrocarbon group having 6 to 14 carbons, or a heterocycle having an oxygen atom, a sulfur atom, or a nitrogen atom as its hetero atom; and ring Z is a monocyclic alicyclic carbon ring having 3 to 30 members or a bridged carbon ring having from two to six rings.

4. The compound of claim 2 which is 3-(3,5-dimethyladamant-1-yl)malate.

5. The compound of claim 2 which is dimethyl 3-(3,5-dimethyladamant-1-yl)malate.

6. The compound of claim 2 which is dimethyl 3-cyclooctylmalate.

7. The compound of claim 2 which is dimethyl 3-cyclohexylmalate.

8. The oxalacetic acid derivative of claim 1, represented by the following formula (1):

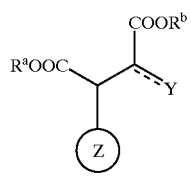

(1)

wherein each of $R^a$ and $R^b$ is independently a hydrogen atom, a metal atom, or a hydrocarbon or heterocyclic group; and ring Z is a bridged carbon or a monocyclic carbon ring having eight or more members and Y is an oxygen atom.

9. The oxalacetic acid derivative of claim 8, wherein each of $R^a$ and $R^b$ is independently a hydrogen atom, a metal atom, a straight-chain or branched aliphatic hydrocarbon group having 1 to 20 carbon atom, an alicyclic hydrocarbon group having 3 to 20 carbon atoms, an aromatic hydrocarbon group having 6 to 14 carbons, or a heterocycle having an oxygen atom, a sulfur atom, or a nitrogen atom as its hetero atom; and ring Z is a bridged carbon ring or a monocyclic carbon ring having 8 to 30 members.

10. The compound of claim 8 which is 3-(3,5-dimethyladamant-1-yl)oxalacetate.

11. The compound of claim 8 which is dimethyl 3-(3,5-dimethyladamant-1-yl)oxalacetate.

12. The compound of claim 8 which is dimethyl 3-cyclooctyloxalacetate.

13. The compound of claim 8 which is dimethyl 3-cyclohexyloxalacetate.

* * * * *